United States Patent [19]
Shigemori

[11] Patent Number: 5,469,264
[45] Date of Patent: Nov. 21, 1995

[54] OPTICAL MEASUREMENT APPARATUS

[75] Inventor: Kazuhisa Shigemori, Kouga, Japan

[73] Assignee: Daikin Industries, Ltd., Osaka, Japan

[21] Appl. No.: 244,665

[22] PCT Filed: Oct. 6, 1993

[86] PCT No.: PCT/JP93/01441

§ 371 Date: Jul. 7, 1994

§ 102(e) Date: Jul. 7, 1994

[87] PCT Pub. No.: WO94/08227

PCT Pub. Date: Apr. 14, 1994

[30] Foreign Application Priority Data

Oct. 7, 1992 [JP] Japan .................................. 4-268791

[51] Int. Cl.⁶ .................................................. G01N 21/25
[52] U.S. Cl. .................................................. 356/417; 356/440
[58] Field of Search .................................. 356/417, 440, 356/361

[56] References Cited

U.S. PATENT DOCUMENTS 4,810,658  3/1989  Shanks et al. ................ 356/440 X

FOREIGN PATENT DOCUMENTS 61-502418  10/1986  Japan .
0208730  8/1988  Japan ............................ 356/301
2-25749  1/1990  Japan .
4-255144  8/1992  Japan .
4-262244  9/1992  Japan .

Primary Examiner—Vincent P. McGraw
Assistant Examiner—K. P. Hantis
Attorney, Agent, or Firm—Beveridge, DeGrandi, Weilacher & Young

[57]  ABSTRACT

An optical measurement apparatus in which a reaction vessel is formed on a surface of at least one side of an optical waveguide, and which apparatus includes a signal light outgoing section for outgoing a signal light which is obtained by introducing a measurement light in the optical waveguide, and a detection section for detecting the signal light from the signal light outgoing section is described. The optical measurement apparatus for preventing stray light further includes a preventing device, positioned near the signal light outgoing section, for preventing stray light, which is outgone from an interior of the reaction vessel to an edge section of the signal outgoing section, from being guided to a detection region of the detection section. The stray light, which has a same wavelength to that of the signal light, is thus prevented from reaching the detection device by the preventing device.

12 Claims, 7 Drawing Sheets

OPTICAL MEASUREMENT APPARATUS

TECHNICAL FIELD

This invention relates to an optical measurement apparatus. More particularly, this invention relates to an optical measurement apparatus in which a reaction vessel is formed on a surface at one side of a slab-type optical waveguide, a measurement light is introduced in the slab-type optical waveguide through a prism, and a signal light is outgone or sent out through the slab-type optical waveguide and the prism. The signal light dependent upon the optical characteristics that exist in the vicinity of the surface at one side of the slab-type optical waveguide.

BACKGROUND ART

From the past, an optical measurement method is known in which a slab-type optical waveguide is employed, and wherein only a labeled fluorescent substance, existing in the vicinity of a surface of the slab-type optical waveguide, is excited by an evanescent wave component scarcely penetrating from the slab-type optical waveguide, and existence or non-existence of immunoreaction, or degree of immunoreaction, is measured based upon the excited fluorescent light. To actualize the method, an apparatus which is shown in FIG. 10 is proposed (refer to Swiss Patent Specification No. 2799/85-2, and an official gazette of Tokukaisho No. 63-273040). In the apparatus, a reaction vessel 92 is formed in one body on one face of a slab-type optical waveguide 91 which has a prism at an edge portion for light introduction. An exciting light sent from a laser light source or the like, which is not shown, is introduced in the slab-type optical waveguide 91 through a dichroic mirror 93. Fluorescent light radiated from labeled fluorescent substance is sent through the slab-type optical waveguide 11, and the outgone fluorescent light is separated from an exciting light path by the dichroic mirror 93, and the outgone fluorescent light is incident on an optical detector 95 through an optical filter 94.

When the above-mentioned arrangement is employed, for example, antibodies 96 are previously immobilized to the surface of the slab-type optical waveguide 91, antigens 97 in a test liquid are received by the antibodies 96, fluorescent labeled antibodies 98, which are formed by labeling antibodies with fluorescent substance, are further received by the received antigens 97. That is, the quantity of the received fluorescent labeled antibodies 98 is determined based upon the quantity of the antigens 97 in the test liquid. And, only the label fluorescent substance 98a of the received fluorescent labeled antibodies 98 are excited so as to generate fluorescent light by the evanescent wave component which is obtained by introducing an exciting light in the slab-type optical waveguide 91. Therefore, the radiated fluorescent light intensity is in proportion to the quantity of the antigens 97 in the test liquid. The fluorescent light is guided in the slab-type optical waveguide 91.

Consequently the existence or non-existence of an immunoreaction, or degree of immunoreaction, is measured by reflecting only fluorescent light guided through the slab-type optical waveguide 91 by the dichroic mirror 93 and which is incident on the optical detector 95 following screening out the noise light component with the optical filter 94.

But, a part of the exciting-light becomes leaking light so as to excite labeled fluorescent substance 98a even at a position sufficiently apart from the surface of the slab-type optical waveguide 91, because the slab-type optical waveguide 91 has surface irregularity (surface roughness, disfigurement) and the like.

Meanwhile, fluorescent light which is radiated from the labeled fluorescent substance 98a sufficiently apart from the surface of the slab-type optical waveguide 91, is not introduced in the slab-type optical waveguide 91 by a angle more than an critical angle. But, when the distance between the labeled fluorescent substance 98a and the surface of the slab-type optical waveguide 91 becomes nearly equal to the wavelength, the fluorescent light component of which the introduction angle is more than the critical angle increases. Therefore, the fluorescent light guided in the slab-type optical waveguide 91 has sufficient non-sensitivity to fluorescent light other than the fluorescent light radiated in the vicinity of the surface of the slab-type optical waveguide 91.

But, though the fluorescent substance 98a, excited at a position sufficiently apart from the surface of the slab-type optical waveguide 91, radiates non-directional fluorescent light, a part of the fluorescent light is incident on the optical detector 95 through an edge portion of the prism section, side walls of the reaction vessel 92 and the like. More particularly, when the field of view for detection of the optical detector 95 is positioned so as to receive only the fluorescent light guided in and outgone from the slab-type optical waveguide 91, the fluorescent light that passes through the edge portion of the prism section, the side walls of the reaction vessel 92 and the like is scarcely received by the optical detector 95. Such positioning with high accuracy is actually difficult. Even when such positioning with high accuracy is performed, dislocation of the determined positioning caused by vibration and the like of the apparatus should be taken into consideration. Thus, the field of view for detection of the optical detector 95 should be determined to be wide, and the fluorescent light that passes through the edge portion of the prism section, side walls of the reaction vessel 92 and the like is received by the optical detector 95. And, the fluorescent light is not influenced by the optical filter 94, and is received by the optical detector 95 as it is. Therefore the measurement accuracy is lowered.

In the foregoing, description was made only in the case that optical measurement (fluorescent immunity measurement) in the vicinity of the surface of the slab-type optical waveguide 91 is carried out based upon fluorescent light. When optical measurement in the vicinity of the surface of the slab-type optical waveguide is carried out based upon light other than fluorescent light, for example, phosphorescence, the similar disadvantages arise.

DISCLOSURE OF THE INVENTION

This invention was made to solve the above-mentioned problems.

It is an object of this invention to supply an optical measurement apparatus which prevents stray light from being incident on an optical detector, with high accuracy.

To perform the object above-mentioned, an optical measurement apparatus is provided in which a reaction vessel is formed on a surface side of at least one side of a slab-type optical waveguide, and which apparatus includes a signal light sending out section for outgoing a signal light which is obtained by introducing a measurement light in the slab-type optical waveguide. This first embodiment of the invention includes a detection section for detecting the signal light from the signal light outgoing section, and a preventing means for preventing a light component, which is outgone from an interior of the reaction vessel to an edge section of the signal light outgoing section, from being guided to a detection region of the detection section. The preventing means is positioned near the signal light outgoing section. Where, the preventing means may be means for reflecting the light component, may be means for refracting the light component, or may be means for preventing the light component from penetrating.

One embodiment of the optical measurement apparatus of the present invention employs a first prism for noise reduction as the preventing means. The first prism guides the light component, which is outgone from an interior of the reaction vessel to an edge section of the signal light outgoing section, to a location outward of the detection region of the detection section.

The present invention includes an apparatus in which the signal light outgoing section is constituted by a prism for sending out signal light. This outgoing prism has an outgoing face for outgoing the signal light to the detection region of the detection section. In addition to the outgoing prism, a first noise reduction or prevention prism is employed, which prism has an inclined face which has an inclination that is in reverse to the outgoing face of the prism for outgoing signal light with respect to an optical axis of the slab-type optical waveguide.

The present invention further includes an optical measurement apparatus in which the signal light outgoing section also represents or defines the initial measurement light introduction section for introducing the measurement light in the slab-type optical waveguide.

An optical waveguide according to the invention further includes a second prism for noise reduction. This second prism has an inclined face which has the same inclination and is on the same side as the outgoing face of the prism for outgoing signal light. The inclined face represents an extension of the inclined face of the first prism for noise reduction which inclined face of the first prism has inclination that is in reverse to the outgoing face of the prism for outgoing signal light, and further includes a light screening member for performing positioning of the slab-type optical waveguide by being engaged with a concave portion which is formed by the both inclined faces of the first and second noise reduction prisms.

An optical measurement apparatus according to the present invention further includes concave portions for positioning corresponding to the inclined face of the first prism for noise reduction which inclined face has an inclination in reverse to the outgoing face of the prism for outgoing signal light. This embodiment of the present invention further includes a light screening member for performing positioning of the slab-type optical waveguide by being engaged with the concave portions for positioning.

In the present invention when the measurement light is introduced in the slab-type optical waveguide and is guided by being totally reflected, the signal light, depending upon the optical characteristics in the vicinity of the surface of the slab-type optical waveguide, and the measurement light are guided in the slab-type optical waveguide and the signal light is outgone through the signal light outgoing section. Thereby, optical measurement in the vicinity of the surface of the slab-type optical waveguide is performed by receiving the signal light outgone through the signal light outgoing section. Though the apparatus includes the preventing means in the neighborhood of the signal light outgoing section, stray light and the like which normally might to be guided to the detection section together with stray light and the like which is generated at positions sufficiently apart from the surface of the slab-type optical waveguide and the like, is refracted, reflected or screened by the preventing means so as to prevent the stray light from being guided to the detection section. Thereby, offset noise light caused by the stray light and the like is greatly reduced so that accuracy of optical measurement is improved.

As to the embodiment described above which employs the first noise reduction prism as the preventing means, stray light and the like which might otherwise be guided to the detection section together with stray light and the like generated at positions sufficiently apart from the surface of the slab-type optical waveguide and the like, is refracted so that the stray light and the like is directed towards positions far from the detection section. Thereby, offset noise light caused by the stray light and the like is greatly reduced so that the accuracy of optical measurement is improved.

As to the optical measurement apparatus described above which has an outgoing prism for the signal light outgoing section and the first prism for noise reduction has an inclined face in reverse to the outgoing face of the outgoing prism, outgoing direction of the signal light and outgoing direction of the stray light and the like are maintained remarkably different from one another. Consequently, offset noise light caused by the stray light and the like is greatly reduced so that accuracy of optical measurement is improved.

Since the signal light outgoing section, in the embodiments described above, also defines the measurement light introduction section for introducing the measurement light in the slab-type optical waveguide, it is not necessary to form the signal light outgoing section and the measurement light introduction section separately, and thereby the arrangement of the present invention is simplified.

Though the additional embodiment of the invention described above, further includes the second prism for noise reduction (which second prism has an inclined face with an inclination that is the same side as the outgoing face of the prism for outgoing signal light, and has the inclined face continuing off of the inclined face of the first prism for noise reduction with the latter having an inclination in reverse to the outgoing face of the prism for outgoing signal light), and further includes the light screening member for performing positioning of the slab-type optical waveguide by being engaged with the concave portion which is formed by both the inclined faces, stray light and the like is more securely prevented from being guided to the detection section without increasing the number of members which require accurate positioning.

Through the apparatus described above further includes concave portions for positioning corresponding to the inclined face of the first prism for noise reduction (which inclined face has an inclination in reverse to the outgoing face of the prism for outgoing signal light), and further includes the light screening member for performing positioning of the slab-type optical waveguide by being engaged with the concave portions for positioning, stray light and the like is more securely prevented from being guided to the detection section without increasing the number of members which require accurate positioning, and the screening member is prevented from being placed directly in contact with the prisms so that damage and the like of the prisms is prevented from occurring.

BEST FORMS OF UTILIZING THE INVENTION

Hereinafter, referring to the attached drawings, we explain this invention in detail.

Figure 1:
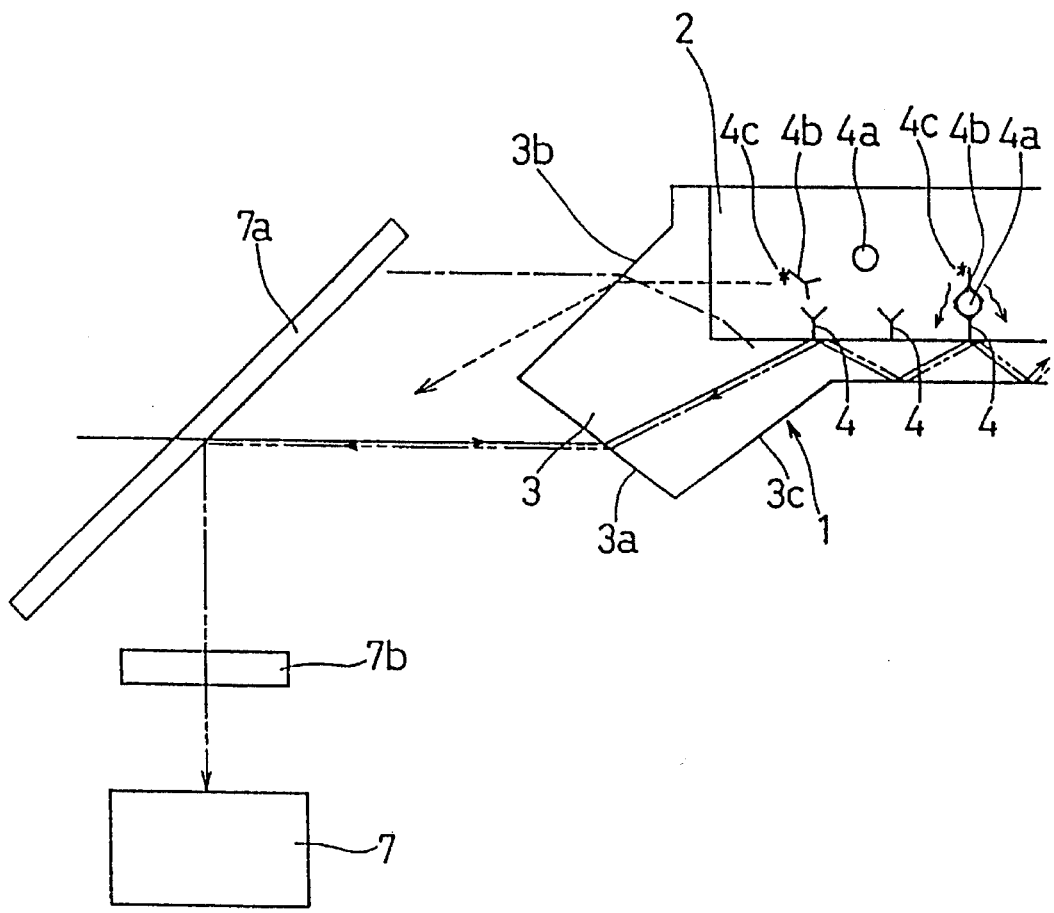
FIG. 1 is a vertical cross section view schematically illustrating a main portion of the optical measurement apparatus of an embodiment according to this invention.

FIG. 1 is a vertical CROSS section view schematically illustrating a main portion of the optical measurement apparatus of an embodiment according to this invention. A reaction vessel 2 is formed in one body to a slab-type optical waveguide 1, and a prism 3 is formed in one body at an edge portion in one side of the slab-type optical waveguide 1. And, the prism 3 includes an introducing-outgoing face 3a for introducing a measurement light in the slab-type optical waveguide 1 in a condition that the measurement light can be totally reflected and for sending out a signal light which is guided in the slab-type optical waveguide 1, and auxiliary faces 3b and 3c, each having inclination reverse to the introducing-outgoing face 3a. Antibodies 4 are previously immobilized to a surface at the reaction vessel 2 side of the slab-type optical waveguide 1. Also, a detector 7 for receiving the signal light is disposed at a predetermined position, the signal light being reflected by a dichroic mirror 7a and being passed through an optical filter 7b.

Operation of the optical measurement apparatus having the above-mentioned arrangement is as follows.

First, the slab-type optical waveguide 1 is positioned to suit an optical axis of an optical system which is not illustrated, and under this condition, antigens 4a in a test liquid are received by the antibodies 4 by pouring the test liquid in the reaction vessel 2. Then, the test liquid is discharged from the reaction vessel 2, and reagent including labeled antibodies 4b which is formed by labeling antibodies with label fluorescent substance 4c is poured in the reaction vessel 2 so that the labeled antibodies 4b are received by the received antigens 4a. That is, the labeled antibodies 4b are bound in vicinity of the surface of the slab-type optical waveguide 1.

In this condition, the label fluorescent substance 4c of the bound labeled antibodies 4b are excited so as to radiate a fluorescent light having a predetermined wavelength by evanescent wave component of a measurement light (refer to a solid line in FIG. 1) which is guided in the slab-type optical waveguide 1. A part of the fluorescent light is introduced in the slab-type optical waveguide 1, is guided by being totally reflected, and is outgone from the introducing-outgoing face 3a of the prism 3 (refer to a two-dot chain line in FIG. 1). Therefore, existence or non-existence of immunoreaction, or degree of immunoreaction is measured by detecting intensity of the outgone fluorescent light with the detector 7.

The above operation is an operation under an ideal condition. In an actual case, a part of the measurement light becomes leaking light caused by irregularity and the like of the surface of the slab-type optical waveguide 1, and the leaking light also excites the label fluorescent substance 4c of the labeled antibodies 4b which float at positions apart from the surface of the slab-type optical waveguide 1 so that excited label fluorescent substance 4c radiate stray fluorescent light which may act as offset noise light. But, the stray fluorescent light is outgone in a direction greatly different from a light path of the fluorescent signal light (e.g., through the auxiliary face 3b), as is illustrated with a dashed line in FIG. 1. Therefore, the stray fluorescent light is easily spacially separated from the fluorescent light as the signal light so that offset noise is greatly reduced, and immunity measurement with high accuracy is performed. Also, introduction of the measurement light in the optical waveguide 1 through the introducing-outgoing face 3a is easily performed which performance is caused by the auxiliary face 3c being formed.

The light path illustrated with a dot chain line in FIG. 1 indicates a limit light path in which the stray fluorescent light is in parallel to the fluorescent light as the signal light. It is understood that most stray fluorescent light is outgone to pass along the above-mentioned light path.

Second Embodiment

Figure 2:
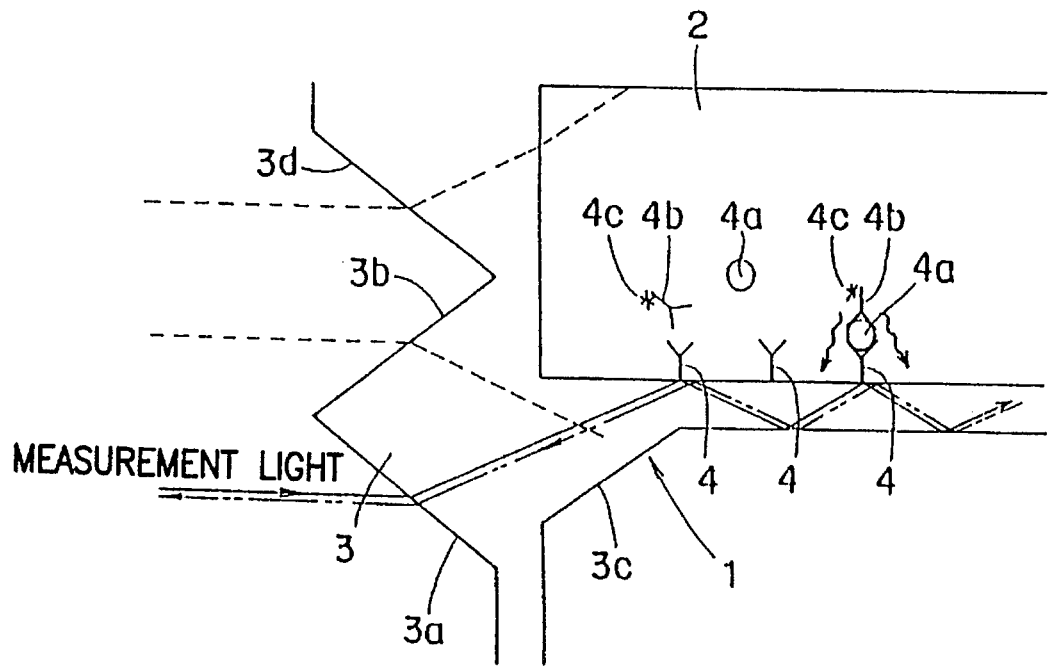
FIG. 2 is a horizontal cross section view illustrating a main portion of the optical measurement apparatus of another embodiment according to this invention.

FIG. 2 is a horizontal cross section view illustrating a main portion of the optical measurement apparatus of another embodiment according to this invention. In this optical measurement apparatus, one side wall of the reaction vessel 2 is assigned as the optical waveguide 1, and the prism having the introducing-outgoing face 3a and the auxiliary face 3b is formed in one body corresponding to the optical waveguide 1, and an auxiliary face 3d is formed in one body which continues the auxiliary face 3b and has the same inclination to the introducing-outgoing face 3a. The auxiliary face 3c is an auxiliary face for easily performing the introduction of the measurement light in the optical waveguide 1 through the introducing-outgoing face 3a.

In this embodiment, stray fluorescent light generated in the interior of the reaction vessel 2 is outgone in a direction greatly different from the light path of the fluorescent light as the signal light by both auxiliary faces 3b and 3d. Therefore, the stray fluorescent light is easily spacially separated from the fluorescent signal light so that offset noise is greatly reduced, and immunity measurement with high accuracy is performed.

The light path illustrated with a dashed line in FIG. 2 indicates a limit light path in which the stray fluorescent light is in parallel to the fluorescent light as the signal light. It is understood that most stray fluorescent light is outgone to pass along the above-mentioned light path.

Third Embodiment

Figure 3:
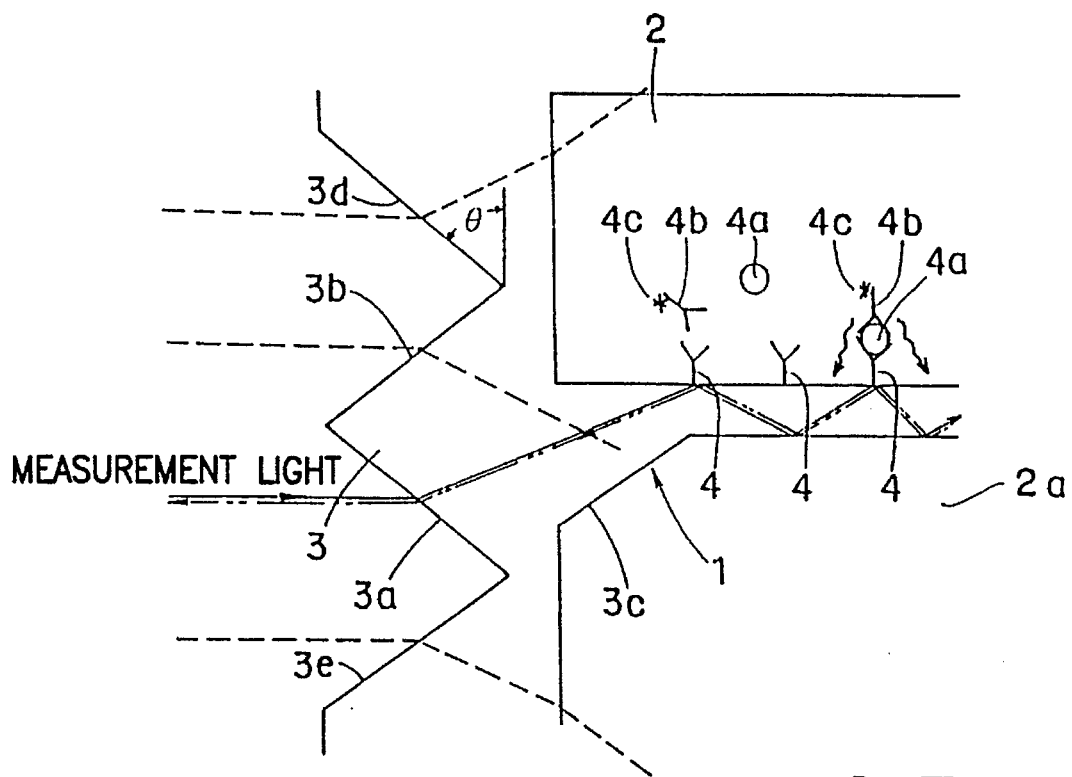
FIG. 3 is a horizontal cross section view illustrating a main portion of the optical measurement apparatus of a further embodiment according to this invention.

FIG. 3 is a horizontal cross section view illustrating a main portion of the optical measurement apparatus of a further embodiment according to this invention. The optical measurement apparatus differs from the embodiment illustrated in FIG. 2 in that another face of the optical waveguide faces a vessel (the vessel may be a vessel for storing dilution liquid and the like, or may be a reaction vessel) $2a$, and in that an auxiliary face $3e$ is formed at a position opposite to the auxiliary face $3b$ with respect to the introducing-outgoing face $3a$.

In this embodiment, stray fluorescent light which may be outgone through the vessel $2a$ or may be generated in the vessel $2a$ is outgone in a direction greatly different from the light path of the fluorescent light as the signal light by the auxiliary face $3e$. Therefore, the stray fluorescent light is easily spacially separated from the fluorescent light as the signal light so that offset noise is greatly reduced, and immunity measurement with high accuracy is performed.

The light path illustrated with a dashed line in FIG. 3 indicates a limit light path in which the stray fluorescent light is in parallel to the fluorescent light as the signal light. It is understood that most stray fluorescent light is outgone to pass along the above-mentioned light path.

Figure 4:
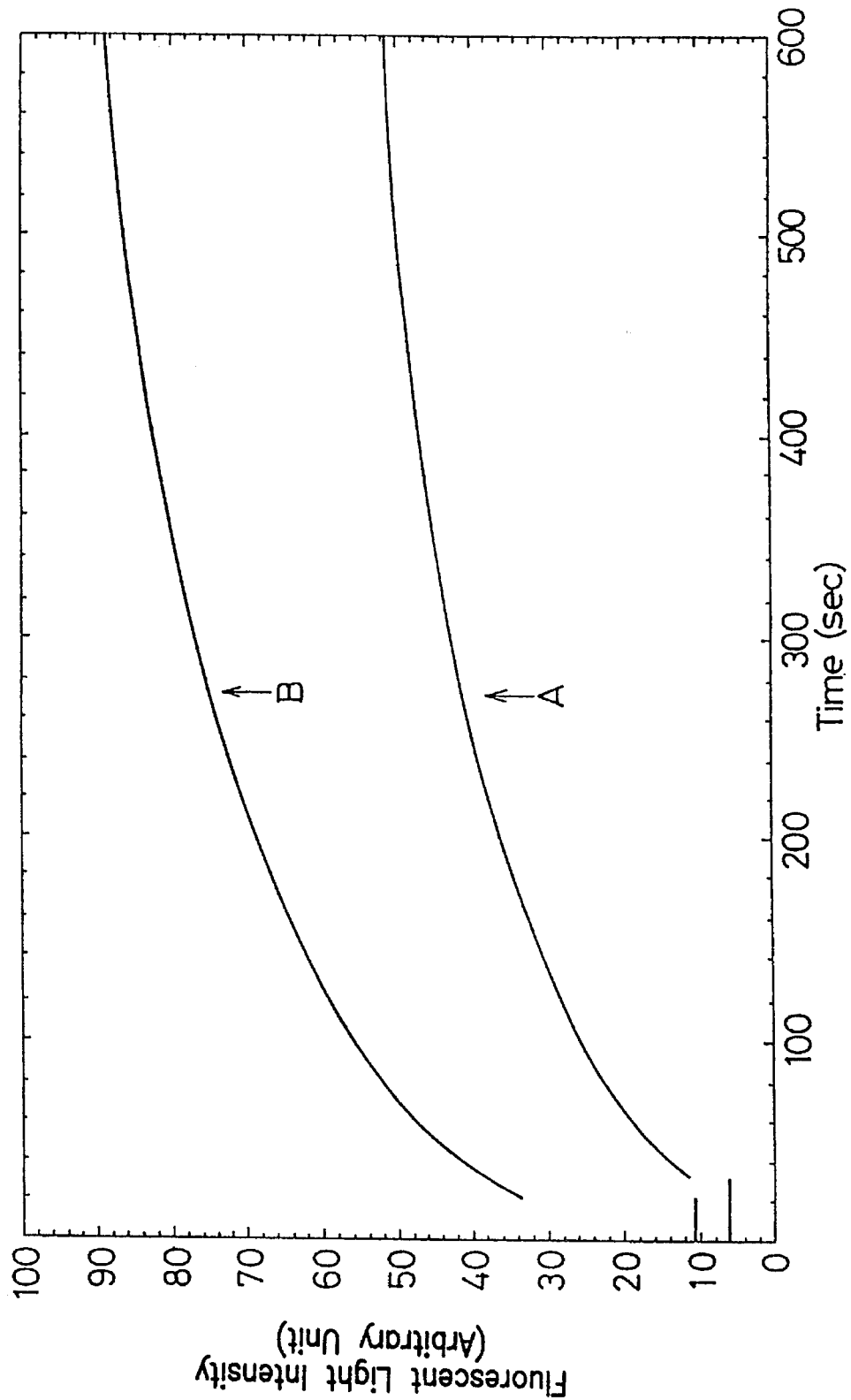
FIG. 4 is a graph illustrating variation following passage of time (refer to A in FIG. 4) of fluorescent light intensity when fluorescent immunity measurement is carried out using the optical measurement apparatus of the embodiment shown in FIG. 3, and variation following passage of time (refer to B in FIG. 4) of fluorescent light intensity when fluorescent immunity measurement is carried out using an optical measurement apparatus in which auxiliary faces 3b and 3d are not formed at all.

FIG. 4 is a graph illustrating variation following passage of time (refer to A in FIG. 4) of fluorescent light intensity when fluorescent immunity measurement is carried out using the optical measurement apparatus of the embodiment shown in FIG. 3, and variation following passage of time (refer to B in FIG. 4) of fluorescent light intensity when fluorescent immunity measurement is carried out using an optical measurement apparatus in which auxiliary faces $3b$ and $3d$ are not formed at all. An angle $\theta$ of the auxiliary face $3d$ of the former optical measurement apparatus is determined to be 60°.

As is apparent from A and B in FIG. 4, signal offsets which are obtained by various stray light caused by the optical measurement apparatus and optical system for light measurement exist from the beginning, but sudden rising of intensity of fluorescent light is observed when labeled antibodies $4b$ are poured and about 20-30 seconds have passed from the beginning of measurement, the sudden raise is caused by there being excited unreacted antigens in the reaction vessel 2, by diffused exciting light and the like. The signal offset is superimposed on a signal fluorescent light during the measurement as a nearly constant offset noise. In the optical measurement apparatus employed for the above measurement, though optimization of a screening prism in which the auxiliary faces $3b$ and $3d$ are assigned as stray fluorescent light outgoing faces, is not performed sufficiently, and though fluorescent light exist a little caused by labeled antibodies $4b$ which exist from the beginning within the reaching extent of the evanescent wave, it is impossible that stray fluorescent light is perfectly screened even when the auxiliary faces $3b$ and $3d$ are formed. But, an increase of the stray fluorescent light at a timing of labeled antibodies $4b$ pouring is reduced to about 1/5.

Figure 5:
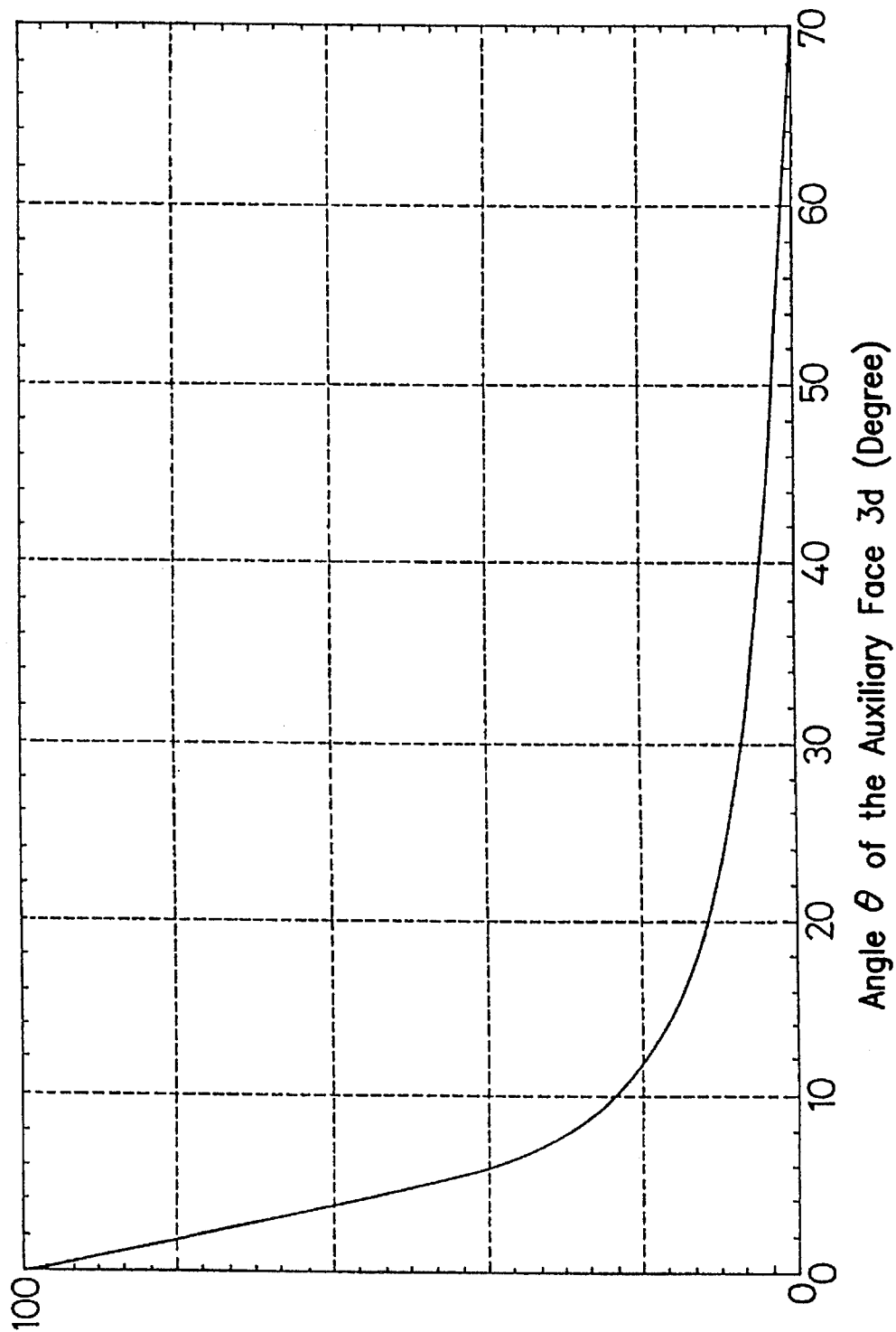
FIG. 5 is a graph illustrating variation of area of a reaction vessel 2 within a field of view of an optical detector when an angle θ of the auxiliary face 3d is varied.

FIG. 5 is a graph illustrating a variation of area of a reaction vessel 2 within a field of view of an optical detector when an angle $\theta$ of the auxiliary face $3d$ is varied. A vertical axis of the graph indicates a ratio to an area in a case that the angle $\theta$ is 0. Calculation of area is performed by a ray tracing calculation. And, refractive index of a liquid in the reaction vessel 2 is assumed to be 1.33, and refractive indexes of the prism and the optical waveguide 1 are assumed to be 1.49, when the calculation is carried out.

In this case, only light parallel to the optical axis is objected for calculation, for simplification.

As is apparent from FIG. 5, the reaction vessel 2 is perfectly screened from the field of view of the optical detector by determining the angle $\theta$ of the auxiliary face $3d$ to be about 70°. But, area of the reaction vessel 2 within the field of view of the optical detector suddenly decreases when the angle of the auxiliary face $3d$ is small, and when the angle $\theta$ of the auxiliary face $3d$ becomes great to some degree (more than about 15°), area of the reaction vessel 2 within the field of view of the optical detector gradually decreases. Therefore, the angle $\theta$ of the auxiliary face $3d$ is sufficiently more than 15° by taking consistency with other parts, formability and the like into consideration.

Fourth Embodiment

Figure 6:
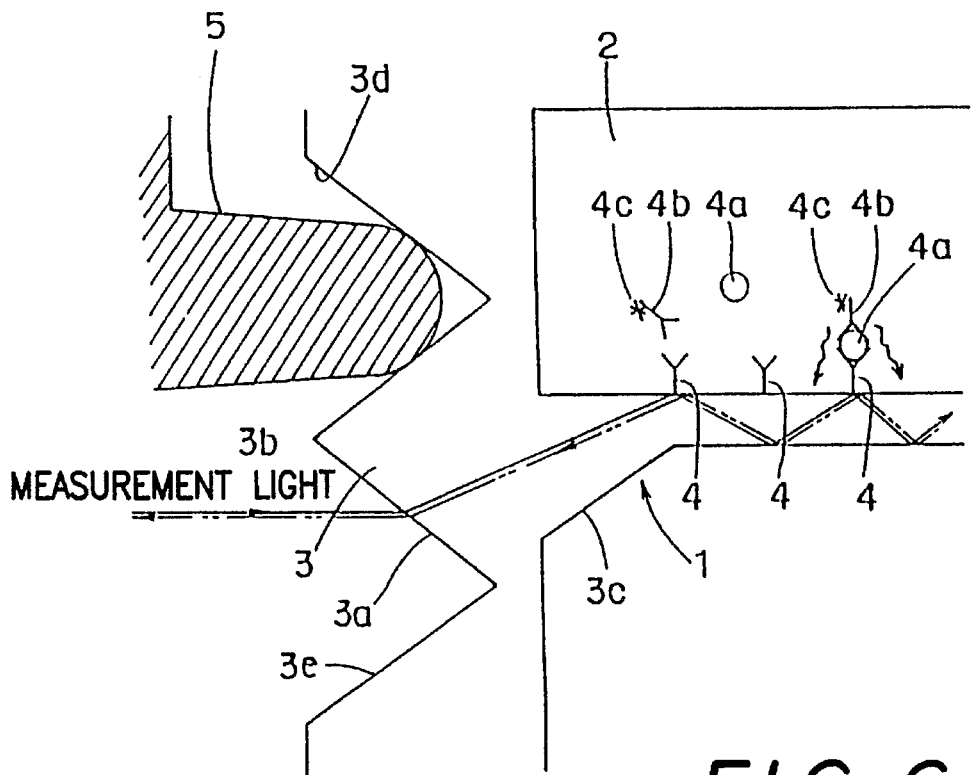
FIG. 6 is a horizontal cross section view illustrating a main portion of the optical measurement apparatus of yet another embodiment according to this invention.

FIG. 6 is a horizontal cross section view illustrating a main portion of the optical measurement apparatus of yet another embodiment according to this invention. The optical measurement apparatus differs from the embodiment illustrated in FIG. 3 in that positioning of the optical waveguide 1 and the prism 3 is performed by engaging a positioning member 5 made of light screening material within the concave portion formed by the auxiliary faces $3b$ and $3d$. The light screening material is exemplified with black colored synthetic resins, for example, but color of synthetic resins is not limited to black, synthetic resins having color which can absorb stray fluorescent light is similarly employable.

In this embodiment, the possibility of stray fluorescent light acting as offset noise light outgone from the auxiliary faces $3b$ and $3d$ is more securely eliminated. Though the positioning member 5 has light screening ability, the apparatus does not need special positioning which apparatus is different from the case where the screening mask is provided separately, the apparatus can thus be simplified in its arrangement.

It is of course possible that screening paint may be coated on a surface of the positioning member 5 instead of forming the positioning member 5 itself with light screening material.

Fifth Embodiment

Figure 7:
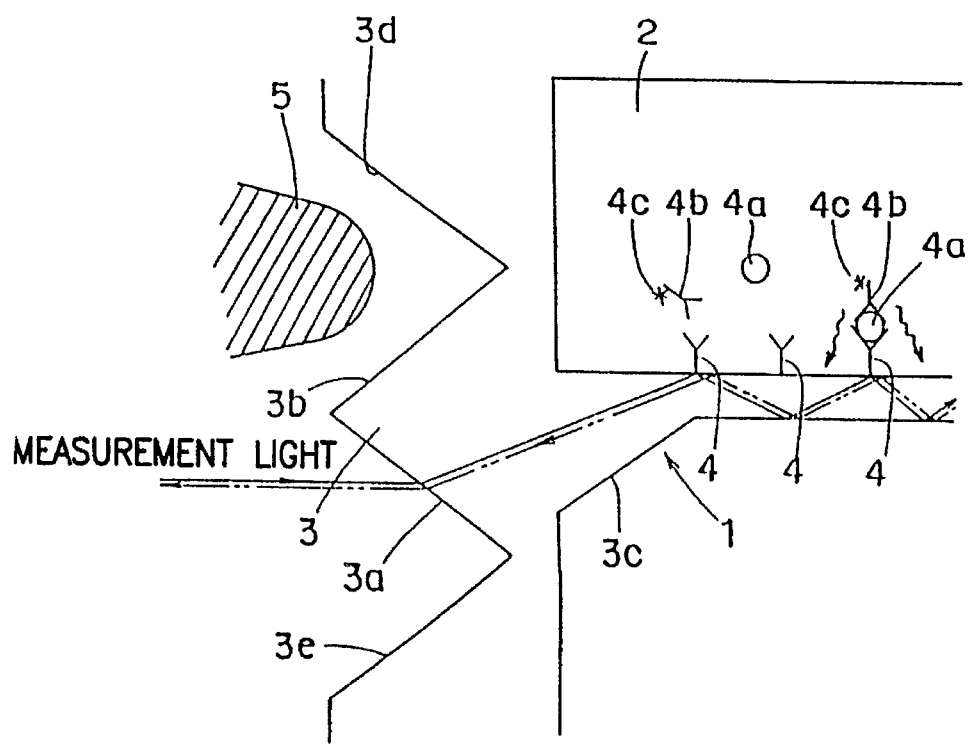
FIG. 7 is a horizontal cross section view illustrating a main portion of the optical measurement apparatus of yet a further embodiment according to this invention.
Figure 8:
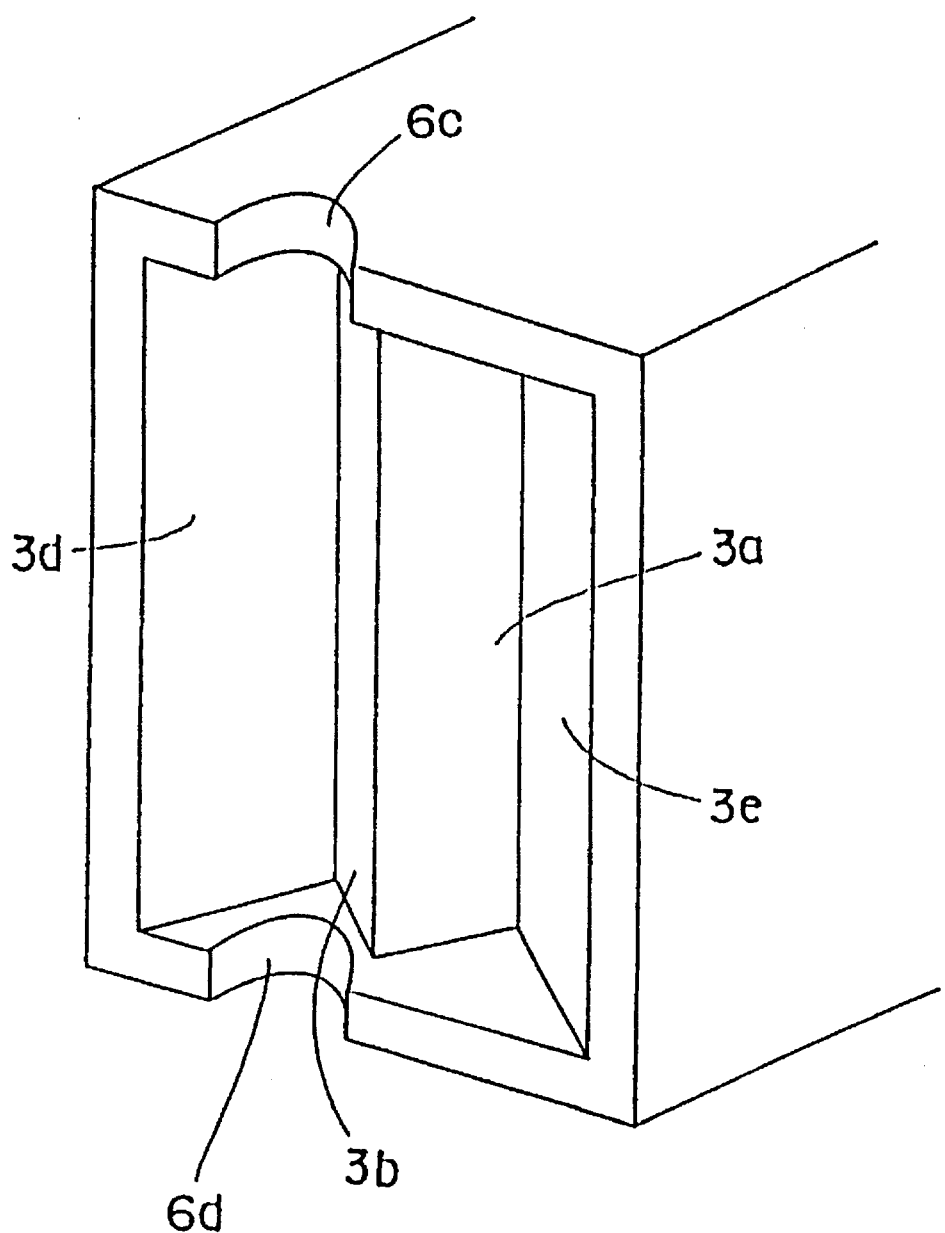
FIG. 8 is a perspective view of a main portion of the above optical measurement apparatus.

FIG. 7 is a horizontal cross section view illustrating a main portion of the optical measurement apparatus of yet a further embodiment according to this invention, and FIG. 8 is a perspective view of a main portion thereof. The optical measurement apparatus differs from the embodiment illustrated in FIG. 6 in that concave portions $6c$ and $6d$ corresponding to the concave portion formed by the auxiliary faces $3b$ and $3d$ are respectively formed on an upper face member $6a$ and a lower face member $6b$ which are formed in one body at an upper edge and a lower edge of the prism 3, and positioning of the optical waveguide 1 and the prism 3 is performed by engaging the positioning member 5 having light screening ability with the concave portions $6c$ and $6d$.

In this embodiment, the positioning member 5 is not pressed to the auxiliary faces $3b$ and $3d$. Consequently, damage and the like of the prism 3 caused by excessiveness of the pressing force and the like is prevented from occurring.

Sixth Embodiment

Figure 9:
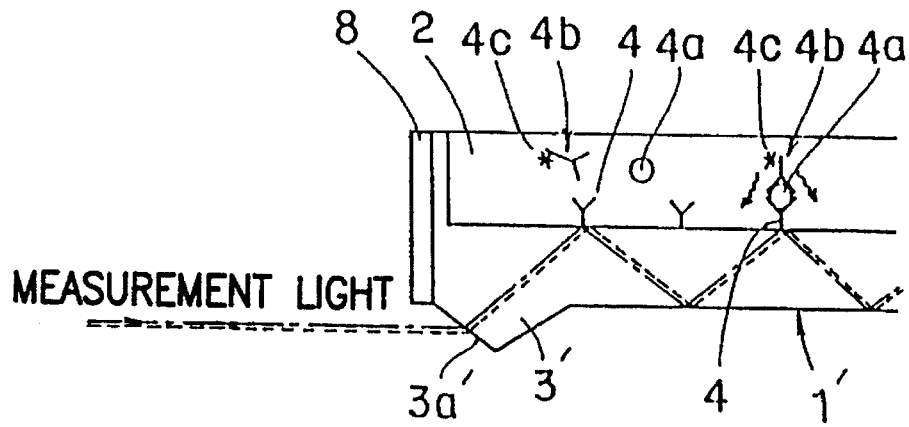
FIG. 9 is a schematic view illustrating a main portion of the optical measurement apparatus of a further embodiment according to this invention.
Figure 10:
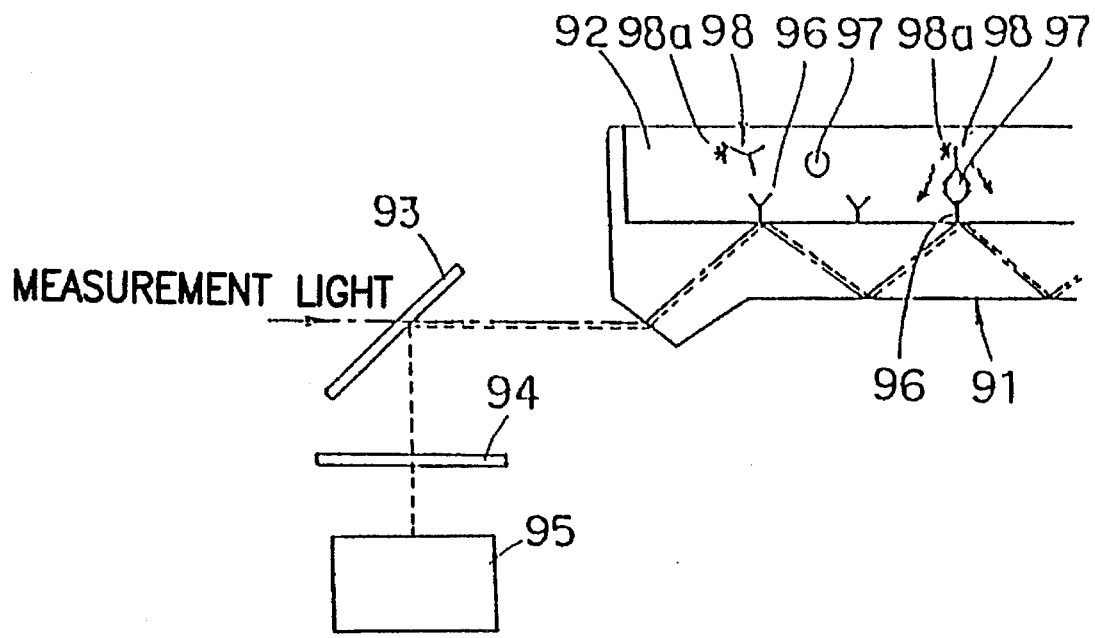
FIG. 10 is a schematic view illustrating a conventional optical measurement apparatus.

FIG. 9 is a schematic view illustrating a main portion of the optical measurement apparatus of a further embodiment according to this invention. The optical measurement apparatus differs from FIG. 10 which illustrates a conventional example in that faces of the apparatus other than the introducing-outgoing face 3a' of the prism 3' and the measurement face of the slab-type optical waveguide 1' are colored 8.

In this embodiment, Stray fluorescent light is screened by the coloring 8, thereby immunity measurement with high accuracy without receiving influence of stray fluorescent light is performed.

In this embodiment, coloring 8 is applied for screening stray fluorescent light, it is of course possible that a light screening mask is disposed instead of coloring 8.

This invention is not limited to the embodiments mentioned above. The invention is applicable to an optical measurement apparatus which outputs phosphorescence and the like as the signal light instead of outputting fluorescent light as the signal light. It is also possible to form the reaction vessel as a separate body with the slab-type optical waveguide. Further, it is possible to apply various modifications to the optical measurement apparatus within the extent which does not change the scope of this invention.

Possibility of Industrial Utilization

This invention is widely applicable to cases in which measurement light is introduced in the slab-type optical waveguide and the signal light is detected so that optical measurement in vicinity of the surface of the slab-type optical waveguide is performed. This invention remarkably reduces influence of stray light and the like which is generated at positions apart from the surface of the slab-type optical waveguide, and the like, so that optical measurement with high accuracy is performed.

What is claimed is:

1. An optical measurement apparatus in which a reaction vessel is formed on a surface of at least one side of an optical waveguide, and which apparatus includes a signal light outgoing section for outgoing a signal light which is obtained by introducing a measurement light in said optical waveguide, and a detection section for detecting the signal light from said signal light outgoing section, the optical measurement apparatus further including preventing means, positioned near said signal light outgoing section, for preventing stray light, which is outgone from an interior of said reaction vessel to an edge section of said signal outgoing section, from being guided to a detection region of said detection section, and wherein said stray light being prevented from reaching said detection device by said preventing means has a same wavelength to that of said signal light.

2. An optical measurement apparatus as set forth in claim 1, wherein said signal light outgoing section (3a)(3a') also defines a measurement light introduction section for introducing measurement light in said optical waveguide (1)(1').

3. An optical measurement apparatus as set forth in claim 1, wherein said preventing means (3b)(3e) includes a first prism for noise reduction which guides the light component which is outgone from the interior of said reaction vessel (2) to an edge section of the signal light outgoing section (3a)(3a'), to outward of a detection region of said detection section (7).

4. An optical measurement apparatus as set forth in claim 3, wherein said signal light outgoing section (3a)(3a') also defines a measurement light introduction section for introducing measurement light in said optical waveguide (1)(1').

5. An optical measurement apparatus as set forth in claim 3, wherein said signal light outgoing section (3a) is constituted by a prism (3a) for outgoing signal light, said prism for outgoing signal light being positioned at an end of said optical waveguide and having an outgoing face for outgoing the signal light to the detection region of said detection section(7), and said first prism (3b)(3e) for noise reduction has an inclined face which has an inclination in reverse to the outgoing face of said prism (3a) for outgoing signal light with respect to an optical axis of said optical waveguide (1), and said first prism for noise reduction extending off from said prism for outgoing signal light.

6. An optical measurement apparatus as set forth in claim 5, wherein said signal light outgoing section (3a) also defines a measurement light introduction section for introducing measurement light in said optical waveguide (1).

7. An optical measurement apparatus as set forth in claim 6, which further includes a second prism (3d) for noise reduction which has an inclined face which has a common inclination to that of the outgoing face of said prism (3a) for outgoing signal light, the inclined face of said second prism continues the inclined face of said first prism (3b) for noise reduction which inclined face of said first prism (3b) is reverse to the outgoing face of said prism (3a) for outgoing signal light, and said optical waveguide further includes a light screening member (5) which is engaged with a concave portion which is formed by the inclined faces of said first and second noise reduction prisms.

8. An optical measurement apparatus as set forth in claim 6, which further includes a light screening member and concave portions (6c)(6d) for positioning said light screening member so as to correspond to the inclined face of said first prism(3b) for noise reduction which inclined face is reverse to the outgoing face of said prism (3a) for outgoing signal light, and said light screening member (5) being adapted for engagement with said concave portions and for performing positioning of said slab-type optical waveguide (1) while being engaged with said concave portions (6c)(6d).

9. An optical measurement apparatus as set forth in claim 1 further comprising a dichroic mirror and an optical filter positioned in a portion of a path of said signal light which portion is downstream from said signal light outgoing section.

10. An optical measurement apparatus as recited in claim 1 wherein said reaction vessel, preventing means, optical waveguide and signal light outgoing section are all formed as a single, unitary body.

11. An optical measurement apparatus in which a reaction vessel is formed on a surface of at least one side of an optical waveguide, and which apparatus includes a signal light outgoing section for outgoing a signal light which is obtained by introducing a measurement light in said optical waveguide, and a detection section for detecting the signal light from said signal light outgoing section, the optical measurement apparatus further including preventing means for preventing stray light, which is outgone from an interior of said reaction vessel, from being guided to a detection region of said detection section, and said preventing means is formed as one body with said optical waveguide, and wherein said stray light being prevented from reaching said detecting device by said preventing means has a same wavelength to that of said signal light.

12. An optical measurement apparatus as set forth in claim 11 further comprising a dichroic mirror and an optical filter positioned in a portion of a path of said signal light which is downstream, in respect to signal light travel, from said signal light outgoing section.

* * * * *